(12) United States Patent
Ray et al.

(10) Patent No.: US 10,307,114 B1
(45) Date of Patent: *Jun. 4, 2019

(54) ITERATIVE VOLUME IMAGE RECONSTRUCTION USING SYNTHETIC PROJECTION IMAGES

(71) Applicant: CARESTREAM HEALTH, INC., Rochester, NY (US)

(72) Inventors: Lawrence A. Ray, Rochester, NY (US); Richard A. Simon, Rochester, NY (US); Levon O. Vogelsang, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/974,812

(22) Filed: May 9, 2018

(51) Int. Cl.
*G06K 9/00* (2006.01)
*A61B 6/03* (2006.01)
*G06T 11/00* (2006.01)
*A61B 6/00* (2006.01)

(52) U.S. Cl.
CPC ............ *A61B 6/032* (2013.01); *A61B 6/5258* (2013.01); *G06T 11/003* (2013.01); *A61B 6/5205* (2013.01); *G06T 2210/41* (2013.01); *G06T 2211/424* (2013.01)

(58) Field of Classification Search
None
See application file for complete search history.

(56) References Cited

U.S. PATENT DOCUMENTS

| 5,270,926 | A | 12/1993 | Tam |
| 5,999,587 | A | 12/1999 | Ning et al. |
| 7,602,879 | B2 | 10/2009 | Chen et al. |
| 9,224,216 | B2 | 12/2015 | Zamyatin et al. |
| 2017/0178316 | A1 | 6/2017 | Simon |
| 2018/0114312 | A1* | 4/2018 | Palma ................... G06T 7/0012 |

OTHER PUBLICATIONS

Matthias Bertram et al. "Directional View Interpolation for Compensation Sparse Angular Sampling in Cone-Beam CT," IEEE Transactions on Medical Imaging, vol. 28, No. 7, Jul. 2009, pp. 1011-1022.
Commonly Assigned U.S. Appl. No. 15/472,613, Entitled: Volume Image Reconstruction Using Projection Decomposition, filed Mar. 29, 2017, by Lawrence A. Ray et al.

* cited by examiner

*Primary Examiner* — Atiba O Fitzpatrick

(57) ABSTRACT

A method for imaging a subject obtains a first set of acquired projection images of a subject volume, wherein each projection image in the first set has a corresponding acquisition angle and forms an initial reconstructed volume image. A second set of synthetic projection images is generated according to processing of the acquired projection images and combined with the first set to form a combined set of projection images. The method augments the initial reconstructed image to form an improved reconstructed image by at least a first iteration of an iterative reconstruction process using the initial reconstructed image with the combined set of acquired and synthetic projection images and at least a subsequent iteration of the iterative reconstruction process using the first set of acquired projection images and fewer than, or none of, the second set of synthetic projection images. The improved reconstruction image is rendered on a display.

12 Claims, 4 Drawing Sheets

# ITERATIVE VOLUME IMAGE RECONSTRUCTION USING SYNTHETIC PROJECTION IMAGES

FIELD OF THE INVENTION

The invention relates generally to the field of diagnostic imaging and in particular to radiographic volume imaging and image reconstruction techniques using computed tomography (CT) and/or cone-beam computed tomography (CBCT).

BACKGROUND OF THE INVENTION

Digital radiographic volume imaging provides three-dimensional (3D) images that have been reconstructed from a series of 2D images taken over a succession of angles of the X-ray source relative to the detector. Acquisition of the 2D projection images used for cone beam CT can employ a large-area digital detector, such as a digital radiography (DR) detector that is typically used for conventional single projection radiography.

Computed tomography (CT) systems, such as cone beam computed tomography (CBCT) or cone beam CT systems offer considerable promise as one type of diagnostic tool for providing 3D volume images. Cone beam CT systems capture volume data sets using a high frame rate flat panel digital radiography (DR) detector and an X-ray source. The X-ray source and detector are typically affixed to a gantry that revolves about the object to be imaged, with the X-ray source directing, from various points along its orbit around the subject, a divergent cone beam of X-rays toward the subject. The CBCT system captures projection images throughout the source-detector orbit, for example, with one 2D projection image at every angular increment of rotation. The projections are then reconstructed into a 3D volume image using various techniques. Among the most common methods for reconstructing the 3D volume image are filtered back projection (FBP) approaches.

While there have been advantages for diagnosis afforded by 3D volume imaging, there are concerns related to repeated patient exposure to x-ray radiation. Various approaches have been proposed with the goal of limiting the number of exposures needed for accurate 3D volume reconstruction and maximizing the amount of information that can be obtained from a set of projection images. However, the number of exposures that are used for reconstruction affects image quality and can also have an impact on the number and severity of image artifacts in the reconstructed 3D volume image. One such artifact, generally termed view aliasing, can have a number of negative effects on the reconstructed volume, such as ripples, for example. View aliasing, well known to those skilled in the imaging arts, occurs when the signal frequency for captured image data exceeds a threshold Nyquist frequency.

Thus, it can be appreciated that there are advantages to image processing and volume reconstruction techniques that can reduce the number and severity of imaging artifacts while allowing imaging with a low level of patient exposure. It can also be appreciated that the processing directly impacts the time required before the volume image can be displayed and that this time can be reduced if intermediate computations can be used effectively.

SUMMARY OF THE INVENTION

It is an object of the present disclosure to advance the art of diagnostic 3D volume imaging and to address deficiencies noted in the background section for reducing patient exposure and reconstruction artifacts.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present disclosure, there is provided a method for imaging a subject comprising: obtaining a first set of N acquired projection images of a subject volume over a range of angles about the subject, wherein each projection image in the first set is acquired at a corresponding acquisition angle; forming an initial reconstructed image of the subject volume from the first set of projection images; generating a second set of M synthetic projection images of the subject volume according to processing of the acquired projection images; combining the first set of N acquired projection images with the second set of M computed synthetic projection images to form a combined set of (N+M) projection images; augmenting the initial reconstructed image of the subject volume to form an improved reconstructed image of the subject volume by executing at least a first iteration of an iterative reconstruction process using the initial reconstructed image with the combined set of (N+M) acquired and synthetic projection images and at least a subsequent iteration of the iterative reconstruction process using the first set of N acquired projection images and fewer than, or none of, the second set of M synthetic projection images; and rendering the improved reconstruction image on a display.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
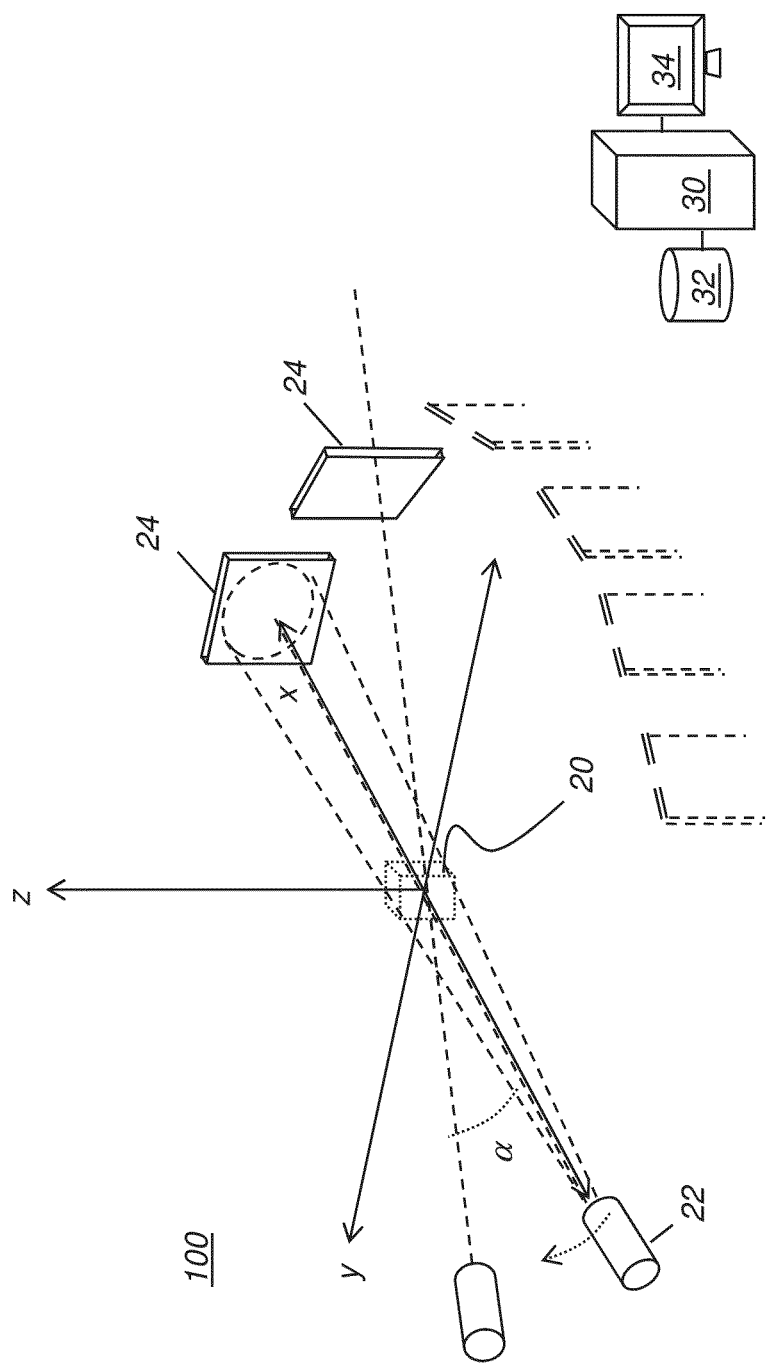
FIG. 1 is a diagram that shows, in schematic form, the scanning activity of a conventional CBCT imaging apparatus.

The following is a detailed description of preferred embodiments of the invention, reference being made to the drawings in which the same reference numerals identify the same elements of structure in each of the several figures.

In the drawings and text that follow, like components are designated with like reference numerals, and similar descriptions concerning components and arrangement or interaction of components already described are omitted.

Where they are used, the terms "first", "second", and so on, do not necessarily denote any ordinal or priority relation, but are simply used to more clearly distinguish one element from another.

In the context of the present disclosure, the term "volume image" is synonymous with the terms "3-Dimensional image" or "3D image". Embodiments of the present disclosure are particularly well suited for acquisition of 2D projection images in dual-energy format that can be used for subsequent reconstruction of 3D image content for the subject anatomy.

In the image processing context of the present disclosure, "rendering" is the active process of generating and forming an image for display and generating the pattern of signals needed for driving the display, thus displaying the image to a user. Image data content that is used for rendering can be transformed from a 2D or 3D model (or models), typically stored as scene content in some type of scene file, into suitable patterns of light energy that are emitted from a display screen. A scene file contains objects in a strictly defined language or data structure, describing aspects of the image content such as geometry, viewpoint, texture, lighting, and shading information as a description of a scene. The data contained in the scene content or scene file is passed to a rendering program to be processed and output or streamed to a display driver or graphics processing unit (GPU) for direct presentation on a display or to a digital image or raster graphics image file. The digital image data file can alternately be available for presentation on a display. In general, the term "rendering" provides a transformation that can be considered as analogous to an "artist's rendering" of a scene; different artists working in different media can generate different renderings of the same scene content. The same image content can be rendered, for example, on a monochrome display or in color on a full color display.

The term "modality" is a term of art that refers to types of imaging. Modalities for an imaging system may be conventional X-ray radiography, fluoroscopy or pulsed radiography, tomosynthesis, tomography, ultrasound, MRI, or other types of imaging. The term "subject" refers to the patient who is being imaged and, in optical terms, can be considered equivalent to the "object" of the corresponding imaging system.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members. For a set S, a subset may comprise the complete set S. A "proper subset" of set S, however, is strictly contained in set S and excludes at least one member of set S. A "partition of a set" is a grouping of the set's elements into non-empty subsets so that every element is included in one and only one of the subsets. Two sets are "disjoint" when they have no element in common.

With respect to an image detector, the term "pixel" refers to a picture element unit cell containing a photo-conversion circuit and related circuitry for converting incident electromagnetic radiation to an electrical signal. For the image processing steps described herein, the terms "pixels" for picture image data elements, conventionally used with respect 2D imaging and image display, and "voxels" for volume image data elements, often used with respect to 3D imaging, can be used interchangeably.

It should be noted that the 3D volume image is itself generated from image data obtained as pixels on a 2D sensor array and displays as a 2D image from some angle of view. Thus, many 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels.

In the context of the present disclosure, "volume imaging" refers to volume radiographic imaging modalities such as computed tomography (CT) or cone-beam computed tomography (CBCT) imaging. Volume imaging methods form a volume 3D image of a subject that can be viewed as a planar slice or plane section taken at a specified depth and angle. As noted previously, volume imaging obtains 3D depth information by changing the relative angle between the X-ray source and the subject for each 2D projection image that is acquired during scanning.

In the context of the present disclosure, the phrase "in signal communication" indicates that two or more devices and/or components are capable of communicating with each other via signals that travel over some type of signal path. Signal communication may be wired or wireless. The signals may be communication, power, data such as image data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

CBCT imaging apparatus and the imaging algorithms used to obtain 3D volume images using such systems are well known in the diagnostic imaging art and are, therefore, not described in detail in the present application. Some exemplary algorithms and approaches for forming 3D volume images from the source 2D images, projection images that are obtained in operation of the CBCT imaging apparatus can be found, for example, in the teachings of U.S. Pat. No. 5,999,587 entitled "Method of and System for Cone-Beam Tomography Reconstruction" to Ning et al. and of U.S. Pat. No. 5,270,926 entitled "Method and Apparatus for Reconstructing a Three-Dimensional Computerized Tomography (CT) Image of an Object from Incomplete Cone Beam Data" to Tam.

Reference is hereby made to U.S. 2017/0178316 entitled "Accelerated Statistical Iterative Reconstruction" (Simon), incorporated herein by reference in its entirety.

Reference is hereby made to commonly assigned U.S. patent application Ser. No. 15/472,613, filed on Mar. 29, 2017, published as U.S. Pat. No. 10,089,758 entitled "Volume Image Reconstruction Using Projection Decomposition" (Ray), incorporated herein by reference in its entirety.

In order to more fully understand the methods of the present invention and the problems addressed, it is helpful to review principles and terminology used for CBCT image capture and reconstruction. Referring to the perspective view of FIG. 1, there is shown, in schematic form and using enlarged distances for clarity of description, the activity of a conventional CBCT imaging apparatus 100 for acquiring the individual 2D images that are used to form a 3D volume image. A cone-beam radiation source 22 directs a cone of radiation toward a subject 20, such as a patient or other subject. A sequence of acquired 2D projection images is obtained in rapid succession at varying angles about the subject, such as one image at each 1-degree angle increment in a 200-degree orbit (α=1°). A digital radiography (DR) detector 24 is moved to different imaging positions about subject 20 in concert with corresponding orbital movement of radiation source 22. FIG. 1 shows a representative sampling of DR detector 24 positions to illustrate how these acquired projection images are obtained relative to the position of subject 20.

Once the needed 2D projection images are captured in this sequence, a suitable imaging algorithm is used for reconstruction of a 3D volume image using the data from the acquired 2D projection images. There are two basic approaches used for reconstruction processing that generates the 3D volume image:

(i) Analytic reconstruction. Analytical reconstruction algorithms such as FBP (filtered back projection) assume that the measurement process and the projection data are represented by continuous functions. Analytic reconstruction operates upon a simplified system model, with a collimated x-ray beam from the x-ray source rotated about the imaged object and with images sequentially acquired at equal angular increments $\Delta\alpha$ in repeated processing. The intensities measured at the detector for each angle $\alpha$ are mathematically expressed as an integral function for the specific angle $\alpha$ and the position of the x-ray source. The reconstruction process, then, is the solution of the resulting integral equations by inversion (back projection). The back projection that describes the propagation of the measured projection data into the image domain is generally combined with a filter that compensates for the effect of low-pass blur due to numerous projections passing through the center and the periphery of an object. FBP is one exemplary implementation of a discrete analytic approach that assumes that CT transmission measurements are linear functions of the attenuation line integrals along the corresponding primary photon trajectories through the subject, and assumes that these measurements are noiseless. When scanning subjects formed of anatomically native materials under normal conditions, relatively simple corrections to the raw projection data are sufficient to assure that these assumptions (i.e. linear relationship) are at least approximately true. This treatment generally allows acquisition and accurate volume reconstruction without visually observable artifacts. Although advantaged for robustness and speed, analytic reconstruction methods can have disappointing results in handling image noise.

(ii) Iterative reconstruction. Iterative reconstruction, described in more detail subsequently, employs algebraic or statistical methods for solving a system of linear equations. The projection data value is modeled as a combination of two attenuation coefficients corresponding to a ray path. The mathematical model for an iterative reconstruction algorithm has a data term and a regularization term (or prior term) that incorporates noise and other non-uniformities of the imaging process. Various weightings can also be introduced, based on factors such as statistical uncertainty for high noise images, for example.

Hybrid techniques have been proposed that combine features of both analytic and iterative processing for improved handling of image noise. However, both analytic and iterative approaches require using the full complement of acquired 2D projection images, with corresponding levels of radiation to the patient.

Image acquisition and program execution are performed by a computer 30 or by a networked group of computers 30 that are in image data signal communication with DR detectors 24. Image processing and storage is performed using a computer-accessible memory 32. The 3D volume image can be rendered for presentation on a display 34.

Embodiments of the present invention can be readily adapted to the particular geometry of the CBCT system or other volume imaging apparatus. For example, an extremity imaging apparatus that is designed to image anatomy such as feet, ankles, knees, and other extremities can generate volume images suitable for application of methods described herein.

In the context of the present disclosure, "acquired" projection images are 2D images captured or obtained from scanning the subject with radiation energy, as was described with reference to FIG. 1. "Synthetic" or "synthesized" projection images are 2D images calculated or generated by the system, using data obtained from the acquired projection images. Various methods can be used for generating synthetic projection images, including interpolation methods as well as the use of forward projection through the reconstructed object at intermediate angles between the angles used for acquired 2D projections.

Reference is hereby made to an article by Bertram, Wiegert, Schafer, Rose, and Aach entitled "Directional View Interpolation for Compensation of Sparse Angular Sampling in Cone Beam CT" in *IEEE Transactions on Medical Imaging* Vol. 28, No. 7, July 2009, pp. 1011-1022.

Reference is hereby made to U.S. Pat. No. 7,602,879 (Chen), and to U.S. Pat. No. 9,224,216 (Zamyatin), both incorporated herein by reference in their entirety.

In typical applications, a computer or other type of dedicated logic processor for obtaining, processing, and storing image data is part of the CT or CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice the method according to the present invention.

Iterative Reconstruction Overview

As noted previously, the class of reconstruction algorithms included under the broad heading of iterative algebraic algorithms offers some improvement over the analytical approach of FBP and similar reconstruction algorithms. Iterative methods use a set of components for iteratively approximating an image f based on the following components:

(i) a model for the image, generally a discretization as discrete voxels;

(ii) a system model that relates the image to acquired image data from a particular imaging apparatus;

(iii) a model for the data that describes statistical relationships between actual and expected measurement values;

(iv) an objective function (or cost function) that defines an acceptable image; and (v) an algorithm that optimizes the objective function in order to closely approximate the actual image (optimization can be a minimization, for example).

The iterative algorithm models the reconstruction as a very large linear system of millions of equations, wherein each pixel for each projection represents an equation and each voxel is an unknown variable. The space of all possible solutions is also the so-called null space of the linear system.

In order for the number of equations to match the number of variables using this approach, the number of projections needed is generally quite large. As a result, there are typically far fewer equations than unknowns. In mathematical terms, this describes an under-determined system. This problem is often approached using a set of assumptions relative to the reconstructed object. For example, the scanned object may be assumed to have few edges and to be substantially smooth. These methods, growing in acceptance, are commonly referred to as variational methods.

However, the solution obtained for an under-determined system using an iterative approach can be one of many possible solutions. The introduction of synthetic projection images yields another possible solution, which can differ from the initial reconstruction by some vector in the null space. In situations where part of the image has fine detail, variational methods often blur the fine detail.

By way of example, but not by limitation, a conventional MBIR (Model-Based Iterative Reconstruction) process can be used to perform iterative reconstruction. MBIR algorithms typically work by first forming an objective function $\Phi$ that incorporates an accurate system model, a statistical noise model, and a prior image model. The image f is reconstructed by computing an estimate f* that minimizes the objective function $\Phi(f)$:

$$\Phi(f) = R(f, \mu(r)) + H(f) \qquad \text{(eq. 1)}$$

$$f^* = \underset{f>0}{\operatorname{argmin}} \Phi(f)$$

wherein:
r represents the spatial coordinate (x,y,z);
H(f) is the data fidelity term;
R(f) is the regularizer/prior image term;
parameter $\mu$ is a scalar that can be a spatially constant or varying parameter that controls the relative effect of the regularizer data and prior term on the final reconstructed image content.

The data fidelity term H(f) encourages the reconstructed object f towards similarity to the original measured noisy projection p data. The regularizer term R(f) constrains the computed reconstruction f to the space defined by the regularizer. The data fidelity term H(f) incorporates a model for the measurement system composed of an accurate system model in a forward projection matrix A; a statistical noise model is incorporated into a statistical weighting matrix W.

A common choice for the data fidelity term is in a quadratic form, as follows:

$$H(f) = \frac{1}{2}(Af-p)^T W(Af-p) = \frac{1}{2}\|Af-p\|_w^2 \qquad \text{(eq. 2)}$$

wherein A is an M×N matrix; $p=(p_1, p_1, \Lambda\, p_M)$ is a vector of length M, and $f=(f_1, f_1, \Lambda\, f_N)$ is a vector of length N.

The statistical weighting matrix W in eq. 2 is inversely proportional to the covariances of the measured projection data p. The covariances are related to the captured photon statistics and preprocessing steps such as detector response and normalization, scatter and beam hardening correction, denoising of the measured projections, and the like. If the measurements are independent, the statistical weighting matrix W is a diagonal matrix with diagonal elements $w_i$ given by:

$$w_i = \frac{1}{\sigma^2(p_i)} \qquad \text{(eq. 3)}$$

wherein $\sigma^2(p_i)$ is the variance of ith projection measurement $p_i$. By way of example, the statistical variance for a Poisson measurement process with independent electronic noise is given by:

$$\sigma^2(p_i) = \frac{I_i + \sigma_e^2}{I_i^2} = \frac{1}{I_{i0}}\exp(p_i)\left(1 + \frac{\sigma_e^2}{I_{i0}}\exp(p_i)\right) \qquad \text{(eq. 4)}$$

wherein $I_{i0}$ is the open field intensity; $I_i$ is the intensity of the ith projection measurement; $p_i = -\log(I_i/I_{i0})$ is the density for the ith ray; and $\sigma_e^2$ is the variance of the sensing electronics.

The regularizer/prior term R(f) constrains (encourages or weights) the reconstructed image f according to prior knowledge about the image content to be reconstructed. Examples of prior knowledge models include smoothness and self similarity within the image, and similarity to a specific prior image or to a class of prior images. Regularizers enforce smoothness in the reconstructed images by constraining neighboring pixels to have similar values.

A number of different algorithms can be used for minimizing the objective function $\Phi(f)$ in f*. One strategy is to utilize so-called forward-backwards operator splitting (aka proximal gradient) methods to minimize the objective function $\Phi(f)$. The operator-splitting technique simplifies and improves the computational efficiency of the minimization by splitting the regularizer term and data fidelity term into the following two step iterative algorithm:

$$(i) \qquad v^{k+1} = f^k - \delta^k A^T W(Af^k - p) \qquad \text{(eqs. 5)}$$

$$(ii) \quad f^{k+1} \leftarrow \underset{f>0}{\operatorname{minarg}}\left\{\mu R(f) + \frac{1}{2\delta^k}\|f - v^{k+1}\|^2\right\}$$

wherein $A^T$ is the transpose of the forward projection matrix A; $\delta$ is a scalar parameter; and k is the iteration index. Value $v^{k+1}$ represents an intermediate reconstructed object at each step in the iteration. The image $f^{k+1}$ represents the regularizer-constrained reconstructed object at each step k in the iteration. Term $\mu R(f)$ indicates varied strength of the preconditioner. The right-most term in the min arg brackets { } is the proximal term. This term encourages the regularizer-constrained reconstructed object $f^{k+1}$ to be close to the intermediate image $v^{k+1}$.

In the above operator-splitting sequence of eqs. 5, step (i) depends only on the choice of forward model A and performs a tomographic update that re-enforces fidelity with the captured data from projections p. This is a gradient descent algorithm where the direction of the gradient, $A^T(Af^k-p)$, and a step size $\delta^k$ are used to update the current image $f^k$. Step (ii) depends only on the choice of regularizer and re-enforces the regularizer on the reconstructed object $v^{k+1}$ from step (i). The two steps iterate until a desired solution is obtained, such as by an optimization of the objective function that is indicative of sufficiently accurate results. The reconstructed image content can then be displayed, stored, or transmitted to another logic processing system or networked computer.

Regularization enforces smoothness in the reconstructed images by encouraging or constraining neighboring pixels to have similar values. Use of regularizers can be considered as a denoising operation, analogous to denoising in other image processing contexts.

In step (i) of eqs. 5, a voxel-independent constant step size $\delta^k$ is used in tomographic update. The global step size $\delta$, applied to each voxel, can be determined empirically, or from the following relationship:

$$0 < \delta < \frac{2}{\|A^T W A\|} \quad \text{(eq. 5.1)}$$

or by the following optimization:

$$\delta^k = \underset{\delta \geq 0}{\operatorname{argmin}}\{H(f^k - \delta A^T W(Af^k - p))\} \quad \text{(eq. 6)}$$

wherein H( ) is the data fidelity term given by eq. 2. The optimization problem can be solved approximately by using a 1-D line search method or in closed form given by:

$$\delta^k = \frac{(\nabla H(f^k))^T (\nabla H(f^k))}{(\nabla H(f^k))^T A^T W A (\nabla H(f^k))} \quad \text{(eq. 7)}$$

Conventional iterative reconstruction algorithms are typically fast in terms of low frequency convergence speed but suffer from slow convergence for high frequencies. Preconditioning methods can be used to accelerate the convergence of the tomographic update step. A preconditioner is a matrix operator that approximates the inverse of the Hessian matrix of the cost function. To help speed convergence, preconditioning induces a coordinate transformation which improves the condition number of the matrix, which determines the relative rate of change of a solution. In a CT reconstruction problem, the preconditioner approach accelerates convergence of high frequency data.

Modifying the Reconstruction Process

Embodiments of the present disclosure provide approaches for reducing patient exposure and reducing view-aliasing artifacts by a modified process that scans and acquires a first set having a number N of actual, acquired projection images that represents only a partial percentage of the full number (N+M) of X-ray projection images that would otherwise be needed to reduce the risk of view aliasing and provide artifact-free reconstruction. An initial reconstruction process is performed using the N projection images, typically using analytic processing. The initial reconstruction is saved to serve as a starting point for subsequent processing using an expanded set of 2D projection images and using a different reconstruction processing method.

To form the expanded set of 2D projection images, the process of the present disclosure computes a second set of M synthetic images, typically generated using the initial reconstruction, as described in more detail following. Processing then combines the first set of N acquired images with the second set of M computed, synthetic images to form the expanded set for further processing.

One or more cycles of iterative processing then executes. The expanded set of (N+M) images is used for at least one iteration of the iterative reconstruction method. Then, as further iterative processing cycles execute, some or all of the M synthetic images are removed from the expanded set. The influence of the synthetic projection images decreases as the acquired N projection images have more influence on the final reconstructed volume. As a result, improved image quality can be obtained for the final volume, particularly in regions of fine detail.

Generating Synthetic Projection Images

Synthetic projection images can be generated using one of several alternative approaches. As shown in the schematic diagram of FIG. 2A, the CBCT scan generates a set of acquired projection images {P1, P2, P3, P4, P5, P6, . . . PN} at a corresponding set of scan angles. Two acquired projection images are considered adjacent when their respective angles are adjacent in sequence, separated by the angular increment $\Delta\alpha$ for scanning as shown in FIG. 1. Thus, with reference to FIG. 2A for example, image P2 is considered adjacent to image P1 and to image P3.

Figure 2A:
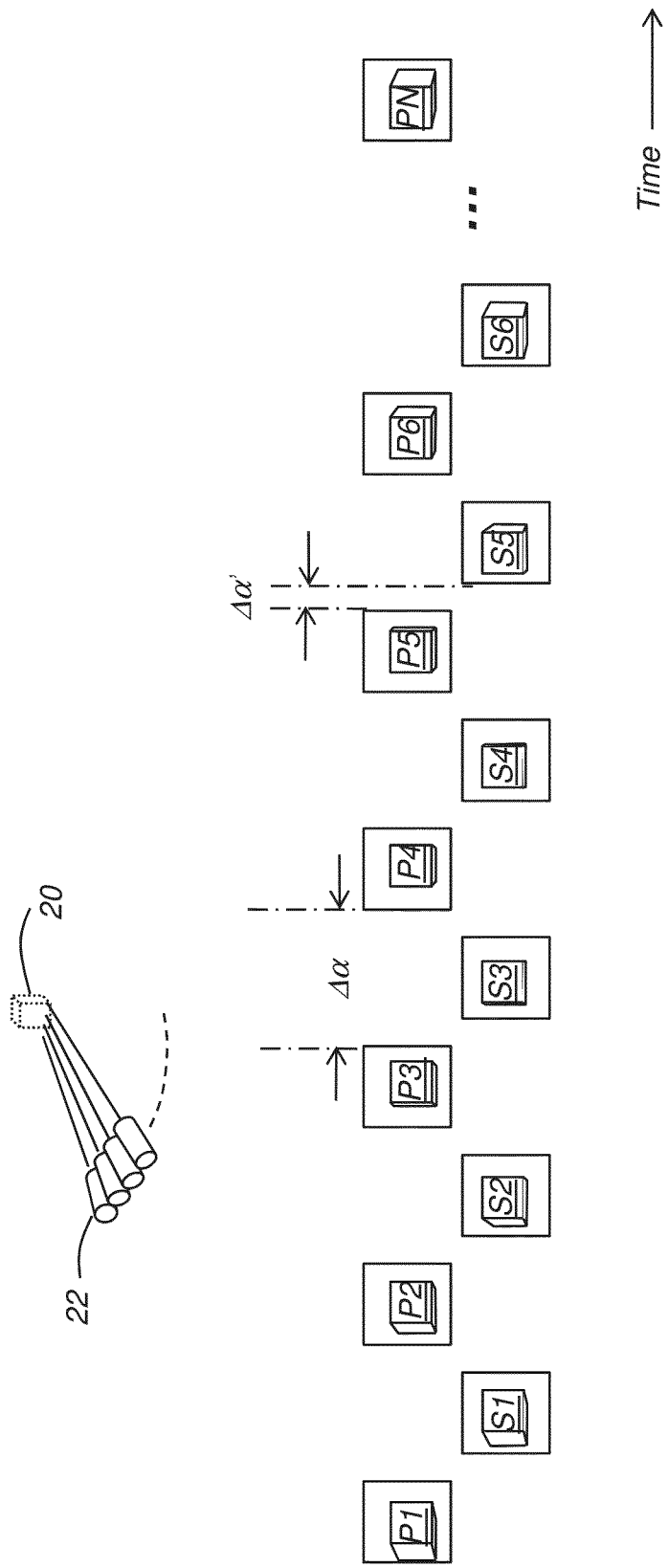
FIG. 2A is a schematic diagram that shows the respective angular ordering that is provided for acquired and synthetic projection images.

A set of synthetic projection images {S1, S2, S3, S4, S5, S6 . . . SN} can be generated to supplement the set of acquired projection images. The synthetic images can be computed for intermediate angles, between the angles spaced $\Delta\alpha$ apart used for the acquired projection images. In this way, a projection image, acquired or synthetic, can be provided at angular intervals of $\Delta\alpha'$ from adjacent acquired or synthetic projection images as shown in FIG. 2A.

Figure 2B:
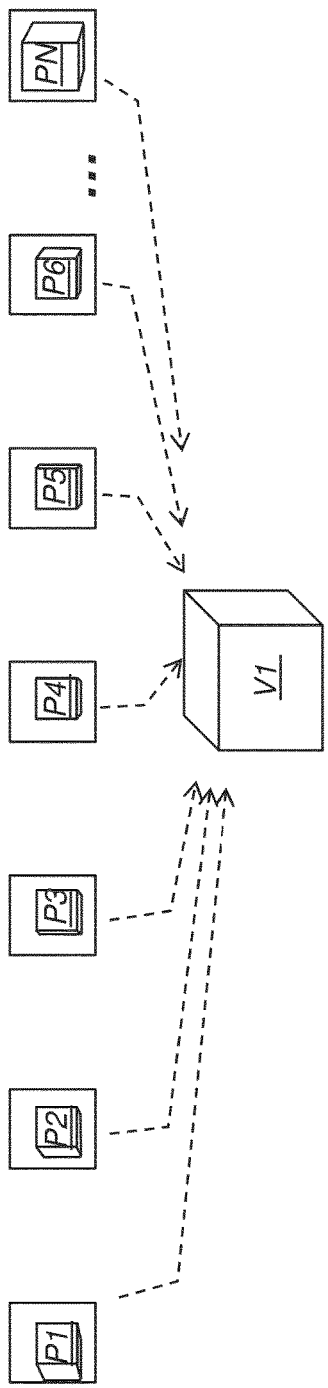
FIG. 2B is a schematic diagram showing generation of a volume image using only acquired projection images.
Figure 2C:
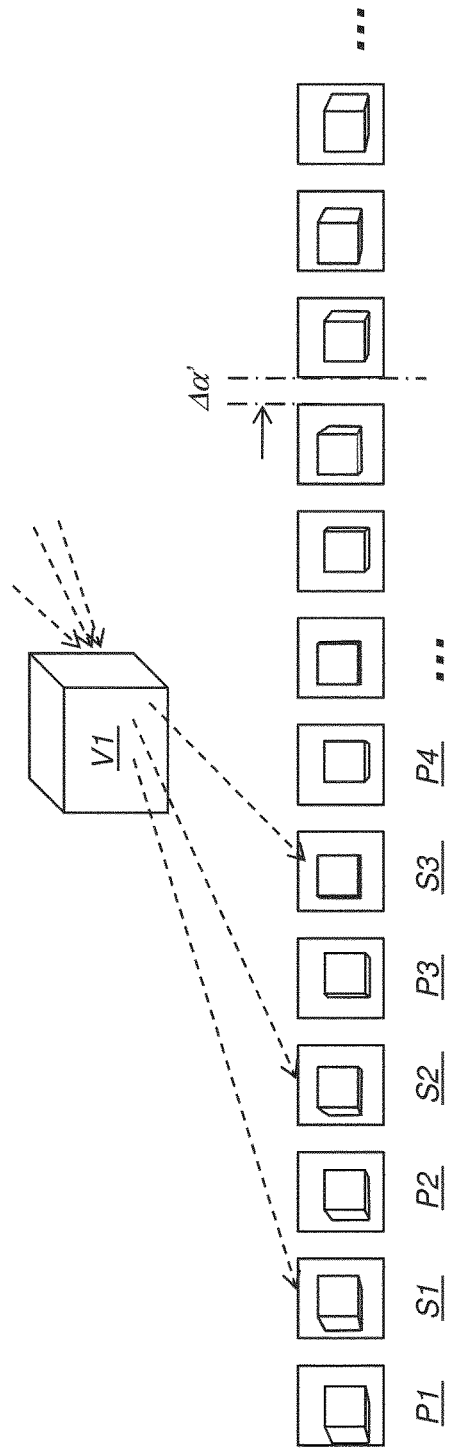
FIG. 2C is a schematic diagram showing generation of a volume image using both acquired and synthetic projection images.

FIGS. 2B and 2C, show how system logic can generate the set of synthetic images using forward projection. An initial volume V1 is generated using analytic reconstruction from a sparse set of projection images taken at widely spaced angles. Forward projection, as shown in FIG. 2C, then calculates a synthetic projection image through the volume V1 at each of a number of intermediate angles n.5$\alpha$ between the acquisition angles n$\alpha$ used for the acquired projection images.

View-aliasing artifacts, resulting from under-sampling, can occur in the reconstructed image when there is insufficient 2-D projection image data for forming the 3-D image with acceptable accuracy. By filling in the gaps and providing projection image data at a larger number of angles, synthetic images can provide some correction for view aliasing.

Reconstruction Processing

Figure 3:
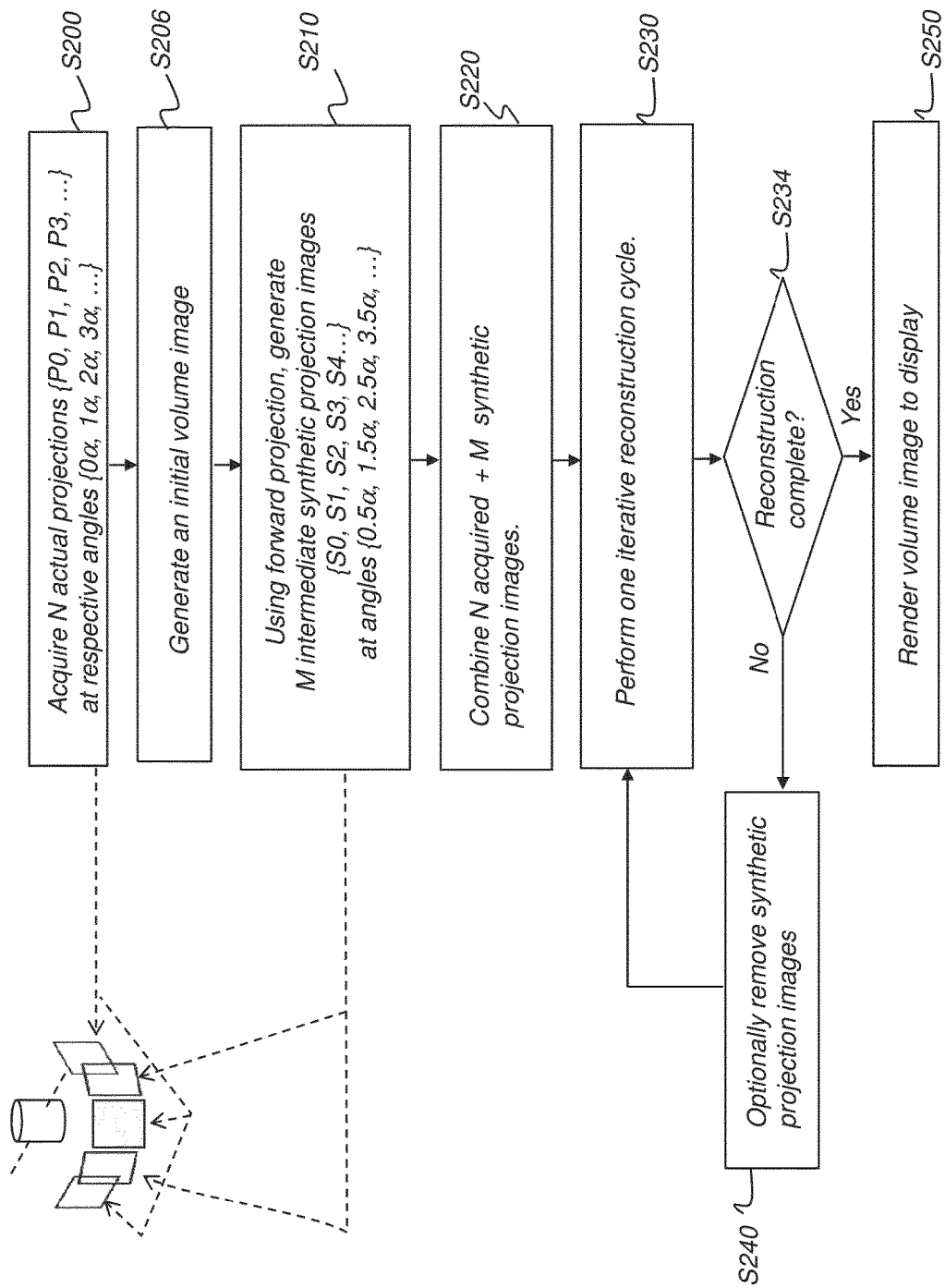
FIG. 3 is a logic flow diagram that shows a sequence for forming a volume image using combined acquired and synthetic projection images according to an embodiment of the present disclosure.

The logic flow diagram of FIG. 3 shows a sequence for improved iterative reconstruction processing according to an embodiment of the present disclosure. In an acquisition step S200, an ordered set having a number N of actual X-ray projection images {P0, P1, P2, P3, . . . }, termed the "acquired" images in the context of the present disclosure, is obtained. Each X-ray projection image in the set is acquired at one of a corresponding sequence of N capture angles $\alpha$ as indicated in FIG. 1. The ordered set of N acquired X-ray projection images can be considered ordered according to acquisition angle n$\alpha$ wherein n represents an integer. In practice, X-ray projection images can be acquired in any order with respect to angle; the ordered set structure is convenient arrangement for showing the acquisition sequence, at an ordered progression of angles, and for illustrating the processing that follows, used to generate synthesized images in a synthetic projection image generation step S210.

Using the set of N acquired projection images, a reconstruction step S206 generates an initial volume image using an analytic reconstruction method such as FBP or FDK (Feldkamp, Davis and Kress) processing. This initial volume image is first used for generating a complementary set of M synthetic projection images. Then, with the combined (N+M) set of acquired plus synthetic projection images, iterative reconstruction processing begins operating upon the initial volume image that has already been generated.

Unlike previous methods that discard the initial volume image once the set of M synthetic images have been generated and perform reconstruction from the beginning using the combined set of images, the Applicants' method does not discard the initial volume image. Instead, the Applicants' method takes advantage of the existing reconstruction data as an intermediate starting point. The Applicants' method uses the added synthetic projection image content, along with the acquired set of N projection images to continue the process, augmenting the initial reconstruction image, changing the processing mode to an iterative processing mode for one or more iterations.

Synthetic projection image generation step S210 calculates data values for each of M intermediate synthetic projection images {S0, S1, S2, S3, S4, . . . } at a corresponding complementary set of intermediate angles {0.5α, 1.5α, 2.5α, 3.5α, 4.5α, . . . }. A combination step S220 adds or otherwise combines the sets of acquired and synthetic projection images to form a combined set of (N+M) projection images for reconstruction.

A reconstruction step S230 starts the next phase of reconstruction using iterative reconstruction logic. Step S230 begins with the combined set of (N+M) projection images generated in step S220 to perform at least one cycle of iterative reconstruction processing, augmenting the initial volume image formed in step S206. When the iterative processing algorithm has completed and the volume image is suitably augmented, a decision step S234 determines whether or not reconstruction processing is completed. Completion can be based on any suitable criterion, such as determined by an optimized objective function, or according to some other threshold calculation for iterative approximation, or according to the number of iterations, for example. If not complete, a refinement step S240 optionally changes the composition of the set of projection images and returns operation to reconstruction step S230 for another iteration cycle.

Refinement step S240 in the FIG. 3 process can eliminate all or some of the synthetic projection images from use in subsequent iterative reconstruction processing. For example, refinement step S240 can allow use of the full combined set, with all (M+N) projection images, for one, two, or more iterations, then remove the M synthetic images completely for one or more additional iterations. This refinement adjustment can be used to lend more weight to the actual, acquired projections as iterative reconstruction proceeds.

Using an adjustment of the number of iterations and of the number of synthetic images used in progressive iterations, the Applicants' method can significantly reduce or eliminate view-aliasing artifacts. This method can also help to reduce image degradation over areas of fine detail, which can otherwise result from use of synthetic projection images.

When reconstruction is complete, a rendering step S250 can then render selected views of the reconstructed volume image to the display.

The sequence outlined in FIG. 3 adapts algebraic or statistical reconstruction techniques to reduce view artifacts while, for the same volume image, acquiring a lower number of projection images that require exposure of the patient. By selectively using synthetic images, then removing the synthetic images from subsequent stages in the iterative reconstruction process, an embodiment of the present disclosure can remove view artifacts that typically result from under-sampling. Advantageously, methods of the present disclosure can provide reconstruction of volume data without perceptible loss of fine detail and contrast in highly detailed regions of the reconstruction.

According to an alternate embodiment, synthetic images can be selectively removed from the set of (N+M) images during reconstruction. This arrangement allows successive iterations to generate and refine the reconstruction using different sets of projection images, supplementing a group of acquired projection images with a variable number of synthetic images. Benefits of this variability can include improvement of detail, suppression of artifacts, and other advantages.

Consistent with one embodiment, the present invention utilizes a computer program with stored instructions that perform on image data accessed from an electronic memory. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including networked processors. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for imaging a subject, comprising:
   accessing a first set of N acquired projection images of a subject volume over a range of angles about the subject, wherein each projection image in the first set is acquired at a corresponding acquisition angle;
   forming an initial reconstructed image of the subject volume from the first set of projection images;
   generating a second set of M synthetic projection images of the subject volume according to processing of the acquired projection images;
   combining the first set of N acquired projection images with the second set of M synthetic projection images to form a combined set of (N+M) projection images;
   augmenting the initial reconstructed image of the subject volume to form an improved reconstructed image of the subject volume by executing at least a first iteration of an iterative reconstruction process using the initial reconstructed image with the combined set of (N+M) projection images and at least a subsequent iteration of the iterative reconstruction process using the first set of N acquired projection images and fewer than, or none of, the second set of M synthetic projection images; and
   rendering the improved reconstruction image of the subject on a display.

2. The method of claim 1 wherein accessing the first set of N projection images comprises acquiring the images using a cone-beam computed tomography system.

3. The method of claim 1 wherein forming the initial reconstructed image comprises using an analytic reconstruction method.

4. The method of claim 3 wherein generating the second set of M synthetic projection images comprises using forward projection through the initial reconstructed image.

5. The method of claim 1 wherein augmenting the initial reconstructed image comprises reducing the number of synthetic projection images with each successive iteration.

6. The method of claim 1 wherein augmenting the initial reconstructed image comprises executing at least one iteration without any synthetic images from the second set.

7. The method of claim 1 wherein generating the second set of M synthetic projection images comprises generating at least one synthetic projection image at an angle that is halfway between two adjacent acquired projection images in the first set.

8. The method of claim 1 further comprising transmitting or storing the improved reconstruction image data.

9. The method of claim 1 wherein forming the improved reconstructed image further comprises testing according to an objective function.

10. A method for imaging a subject, comprising:
    obtaining a first set of N acquired projection images of a subject volume over a range of angles about the subject, wherein each projection image in the first set is acquired at a corresponding acquisition angle;
    forming an initial reconstructed image of the subject volume from the first set of projection images using an analytic reconstruction method;
    generating a second set of M synthetic projection images of the subject volume using forward projection through the initial reconstructed image, wherein one or more of the M synthetic projection images have corresponding angles between adjacent angles of two acquired projection images;
    combining the first set of N acquired projection images with members of the second set of M synthetic projection images to form a combined set of projection images;
    augmenting the initial reconstructed image of the subject volume to form an improved reconstructed image of the subject volume by executing at least a first iteration of an iterative reconstruction process using the initial reconstructed image with the combined set of acquired and synthetic projection images and at least a subsequent iteration of the iterative reconstruction process using the first set of N acquired projection images and fewer than, or none of, the second set of M synthetic projection images; and
    rendering the improved reconstruction image on a display.

11. An imaging method, comprising:
    acquiring a number N of projection images of a subject volume over a range of angles about the subject volume, wherein each projection image is acquired from a cone beam computed tomography system with the radiation source and detector disposed at a corresponding acquisition angle;
    generating a number M of synthetic projection images of the subject volume by processing the N acquired projection images to form an initial reconstruction;
    generating an improved reconstruction of the subject volume by iteratively applying an algebraic reconstruction to the initial reconstruction and varying the number of synthetic projection images used between two or more iterations of the algebraic reconstruction;
    terminating the iterative algebraic reconstruction according to an optimized objective function; and
    displaying, storing, or transmitting the improved reconstruction.

12. The method of claim 11 wherein the iterative algebraic reconstruction is a model-based iterative reconstruction.

* * * * *